United States Patent
Hirschberg et al.

(10) Patent No.: US 11,795,126 B2
(45) Date of Patent: Oct. 24, 2023

(54) UPCYCLING PERFLUOROPOLYMERS INTO FLUORINATED OLEFINS

(71) Applicant: 3M INNOVATIVE PROPERTIES COMPANY, St. Paul, MN (US)

(72) Inventors: Markus E. Hirschberg, Mühldorf (DE); Klaus Hintzer, Kastl (DE); Thomas G. Kolbeck, Burgkirchen (DE); Matthias Wieland, Eggstätt (DE); Peter Bauer, Wittibreut (DE); Achim Schmidt-Rodenkirchen, Bayreuth (DE); Thorsten Gerdes, Eckersdorf (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 17/904,611

(22) PCT Filed: Feb. 19, 2021

(86) PCT No.: PCT/IB2021/051450
§ 371 (c)(1),
(2) Date: Aug. 19, 2022

(87) PCT Pub. No.: WO2021/165923
PCT Pub. Date: Aug. 26, 2021

(65) Prior Publication Data
US 2023/0109030 A1    Apr. 6, 2023

Related U.S. Application Data

(60) Provisional application No. 62/979,767, filed on Feb. 21, 2020.

(51) Int. Cl.
*C07C 17/367* (2006.01)
*B01J 8/08* (2006.01)
*B01J 8/10* (2006.01)
*C08J 11/14* (2006.01)
*C10B 53/07* (2006.01)

(52) U.S. Cl.
CPC ............. *C07C 17/367* (2013.01); *B01J 8/085* (2013.01); *B01J 8/10* (2013.01); *C08J 11/14* (2013.01);
(Continued)

(58) Field of Classification Search
CPC .................................................... C07C 17/367
See application file for complete search history.

(56) References Cited

U.S. PATENT DOCUMENTS

| 3,802,411 A | 4/1974 | Manspeaker |
| 5,432,259 A | 7/1995 | Schottle et al. |

(Continued)

FOREIGN PATENT DOCUMENTS

| GB | 1495297 A | * 12/1977 | ........... C07C 17/367 |
| GB | 1496347 A | 12/1977 | |

(Continued)

OTHER PUBLICATIONS

International Preliminary Report on Patentability Ch II for PCT Application No. PCT/IB2021/051450, dated Jan. 21, 2022, 6 pages.
(Continued)

*Primary Examiner* — Medhanit W Bahta
(74) *Attorney, Agent, or Firm* — Thomas M. Spielbauer

(57) ABSTRACT

Mechanical stirred bed reactors that incorporate a screen are described. Methods of using such reactors to process perfluoropolymers to form perfluorinated olefin monomers are also described. The reactors and methods may be used to upcycle filled perfluorinated materials.

12 Claims, 6 Drawing Sheets

(52) U.S. Cl.
CPC ..... *C10B 53/07* (2013.01); *B01J 2208/00442* (2013.01); *B01J 2208/00867* (2013.01); *B01J 2208/00884* (2013.01); *C08J 2327/12* (2013.01)

(56) References Cited

U.S. PATENT DOCUMENTS

| | | |
|---|---|---|
| 5,503,646 A | 4/1996 | Mckenny et al. |
| 6,797,913 B2 | 9/2004 | Van Der Walt |
| 8,344,190 B2 | 1/2013 | Hintzer et al. |
| 2019/0322940 A1 | 10/2019 | Ruan et al. |

FOREIGN PATENT DOCUMENTS

| | | |
|---|---|---|
| WO | 1988008020 A1 | 10/1988 |
| WO | 2001058840 A2 | 8/2001 |

OTHER PUBLICATIONS

International Search Report for PCT Application No. PCT/IB2021/051450, dated May 21, 2021, 5 pages.
Simon, "Chemical Recycling of Polytetrafluoroethylene by Pyrolysis", 1998, Polymer Degradation and Stability, vol. 62, No. 1, pp. 1-7.
Willert-Porada, "Rückgewinnung Fluorierter Monomere Aus Reststoffen", 2010, Universität Bayreuth, 124 pages.

\* cited by examiner

US 11,795,126 B2

UPCYCLING PERFLUOROPOLYMERS INTO FLUORINATED OLEFINS

CROSS REFERENCE TO RELATED APPLICATIONS

This application is a national stage filing under 35 U.S.C. 371 of PCT/IB2021/051450, filed 19 Feb. 2021, which claims the benefit of U.S. Application No. 62/979,767, filed 21 Feb. 2020, the disclosure of which is incorporated by reference in its/their entirety herein.

FIELD

The present disclosure relates to equipment and methods for converting filled perfluoropolymers, including filled perfluoropolymers, into perfluorinated olefins such as tetrafluoroethylene and hexafluoropropylene.

SUMMARY

Briefly, in one aspect, the present disclosure provides a mechanical stirred bed reactor. The mechanical stirred bed reactor includes a reaction chamber comprising a bottom wall, a side wall connected to and extending from the bottom wall to a top of the side wall; a screen comprising a plurality of openings extending through the screen from an opening entrance at the top side of the screen to an opening exit on the bottom side of the screen, wherein the entrance openings have a minimum dimension of Dmin, wherein the screen is supported above the bottom wall and the reaction chamber has a total reaction volume bounded by the side wall and extending from the screen to the top of the side wall; a bed of beads supported by the screen and filling at least 20% of the total reaction volume, wherein no greater than 5% by mass of the beads have a maximum dimension of less than DB5, wherein DB5 is greater than Dmin; and an agitator positioned within the reaction chamber and surrounded by the beads. The reactor may also include one or more of a discharge port below the screen of the reaction chamber; a first feed system comprising a first conduit connected to a first feed port of the reaction chamber to deliver a material to the bed of beads; a second feed system comprising a second conduit connected to a second feed port of the reaction chamber to deliver a carrier gas through the bed of beads and out the discharge port; and an external heater.

In another aspect, the present disclosure provides methods of converting a filled perfluoropolymer into perfluorinated olefins. Such methods include feeding a perfluoropolymer containing a filler into a reaction chamber comprising (i) a bottom wall, a side wall connected to and extending from the bottom wall to a top of the side wall; (ii) a screen comprising a plurality of openings extending through the screen from an opening entrance at the top side of the screen to an opening exit on the bottom side of the screen, wherein the screen is supported above the bottom wall and the reaction chamber has a total reaction volume bounded by the side wall and extending from the screen to the top of the side wall; (iii) a bed of beads supported by the screen and filling at least 20% of the total reaction volume. The methods also include agitating at least 80 wt. % of the beads while heating the perfluoropolymer to a temperature of at least 450° C. and passing a carrier gas through the beads; decomposing the perfluoropolymer to form perfluorinated olefin monomers and releasing the filler; and collecting the perfluorinated olefin monomers and the fillers below the screen. At least 95 wt. % of the filler has a maximum dimension of no greater than DF95, no greater than 5 wt. % of beads have a maximum dimension of less than DB5; and the minimum dimension of the openings in the screen on the side of the screen supporting the beads is Dmin. The ratio of Dmin over DF95 is at least 5, and the ratio of DB5 over Dmin is at least 1.5.

The details of one or more embodiments of the invention are also set forth in the description below. Other features, objects, and advantages of the invention will be apparent from the description and from the claims.

DETAILED DESCRIPTION

Figure 1:
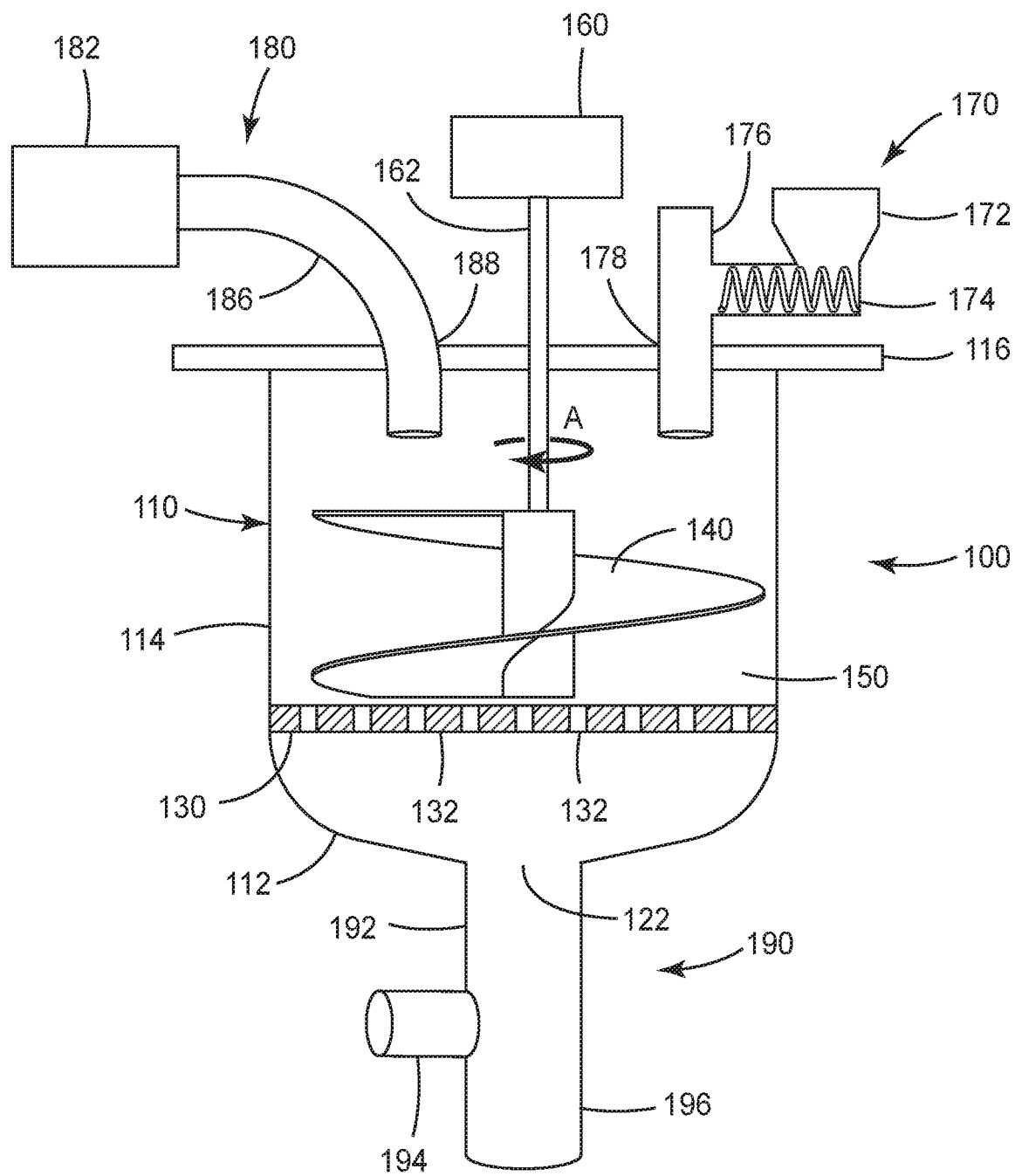
FIG. 1 illustrates an exemplary mechanical stirred bed reactor ("MSBR") according to some embodiments of the present disclosure.

Fluorinated polymers are used in a wide variety of applications. Perfluorinated polymers are particularly useful in demanding applications including those that require high temperature stability or chemical resistance. However, these very properties make recycling challenging. The presence of common fillers such as inorganic fibers (e.g., glass or carbon fibers), carbon, metals and ceramics can make recycling even more difficult. As a result, perfluorinated polymers, particularly filled perfluorinated polymers, may require costly disposal methods.

Many perfluorinated polymers are produced by polymerizing perfluorinated olefins such as tetrafluoroethylene (TFE) and hexafluoropropylene (HFP). However, the generation of the perfluorinated olefins can require difficult procedures and complex reaction conditions to generate raw materials. For example, TFE and HFP can be produced by the pyrolysis of chloro(difluoro)methane (R22) made from trichloromethane and HF at temperatures of 600 to 1000° C. However, this process produces hydrochloric acid as well as partially fluorinated and chlorinated by-products. TFE and HFP can also be produced by electrochemical fluorination methods to avoid the use of low-molecular weight chlorinated raw materials and eliminate the hydrochloric acid waste stream. However, there is still a need for improved equipment and methods of producing perfluorinated olefin monomers.

Co-owned U.S. Pat. No. 8,344,190 ("Process of Making Fluoroolefins by Thermal Decomposition of Fluorinated Materials) describes methods of producing TFE and HFP by the pyrolysis of unfilled fluorinated materials in a carrier gas or a gas fluidized bed. This process of converting fluoropolymer products back into the base monomers used for polymerization is referred to as "upcycling."

Although filled materials may be processed in a fluidized bed reactor, many fillers do not pyrolyze and build up in the fluidized bed. As a result, the efficiency decreases, and the process must be stopped to clean out the reactor. Similar problems arise when using rotary kilns or extruder-type reactors. Thus, there is an on-going need to identify effective methods for upcycling filled perfluoropolymers. For example, there is a need to provide methods for processing filled perfluoropolymers that provide continuous removal of fillers from the reactor while maintaining high yields of the desired perfluorinated olefin monomers.

The present inventors have developed new reactors and methods of upcycling filled perfluoropolymers to produce perfluorinated olefin monomers. The equipment and methods of the present disclosure can be used with a wide variety fluoropolymer feed material. As used herein, the term "perfluoropolymers" includes both polymers having all of the carbon-hydrogen bonds along the backbone replaced with carbon-fluorine bonds, and polymers having some of the carbon-hydrogen bonds along the backbone replaced with carbon-chlorine bonds, with all remaining carbon-hydrogen bonds along the backbone replaced with carbon-fluorine bonds. Such perfluoropolymers may include small amounts of nonfluorinated groups usually associated with initiators or chain transfer agents used in the polymerization reactions, which are not considered as part of the backbone of the polymer. The perfluoropolymers contain repeating units derived from perfluorinated olefins such as tetrafluoroethylene (TFE), hexafluoropropylene (HFP), perfluorinated vinyl ethers (e.g., alkylvinyl ethers), and perfluorinated allyl ethers. In some embodiments, the perfluoropolymers also include repeating units derived from chlorotrifluoroethylene (CTFE).

Examples of perfluorovinyl ethers include those corresponding to the formula:

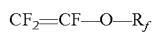

$CF_2=CF-O-R_f$ wherein $R_f$ represents a perfluorinated, linear, cyclic or branched aliphatic group that may contain one or more oxygen atoms. Examples of perfluoroallyl ethers include those that correspond to the formula:

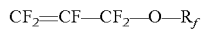

$CF_2=CF-CF_2-O-R_f$ wherein $R_f$ represents a perfluorinated, linear, cyclic or branched aliphatic group that may contain one or more oxygen atoms.

Examples of perfluoropolymers include, but are not limited to, homopolymers of tetrafluoroethylene (PTFE) and copolymers of tetrafluoroethylene, including polymers containing repeating units derived from: TFE and HFP ("FEP"); and TFE and one or more perfluorovinyl and/or perfluoroallyl ethers ("PFA"). The feed material may include more than one fluoropolymer.

Perfluorinated filled polymers, such as PTFE, FEP and PFA, are particularly suited for this process. The perfluorinated polymers can be filled with any of a wide variety of known fillers. In some embodiments, the methods and equipment of the present disclosure are well-suited for processing inorganic fillers, e.g., glass fibers (e.g., those having a diameter of 5-20 μm, and an average length 20-200 μm), glass flakes, solid or hollow glass beads, carbon black, carbon fibers (e.g., those having a diameter of 5-20 μm, and an average length 20-200 μm), graphite, carbons, ceramic materials (e.g. BN, $Al_2O_3$), pigments, metals, and alloys. Typically, the filler content is in the range of 0.01 wt. %-60 wt. %, and often is in the range of 0.1 wt. %-30 wt. %, based on the total weight of the filled fluoropolymer.

The feed can come from virgin compounds (e.g., internal recycling from production processes). However, the equipment and methods of the present disclosure can also be used to recycle waste materials (e.g., after their useful life) such as tubes, films, hoses, bearings, seals, electrodes, and parts. Both sintered and non-sintered materials can be used as feed material.

Materials can be processed (e.g., ground) to generate the desired feed particle sizes. The particle size of the feed material can be selected to meet reactor design requirements. For example, faster pyrolysis and processing rates may be achieved with smaller particle sizes. Typically, the feed materials may vary in size from 50 μm-10 mm. Used fluoropolymer articles may be pre-treated prior to being used as a feed material, e.g., to remove oil or dirt. In some embodiments, partially fluorinated materials may be pre-treated with a fluorination step where fluorine gas is used to convert hydrogen bonds into C—F bonds and generate perfluorinated feed materials.

Figure 2:
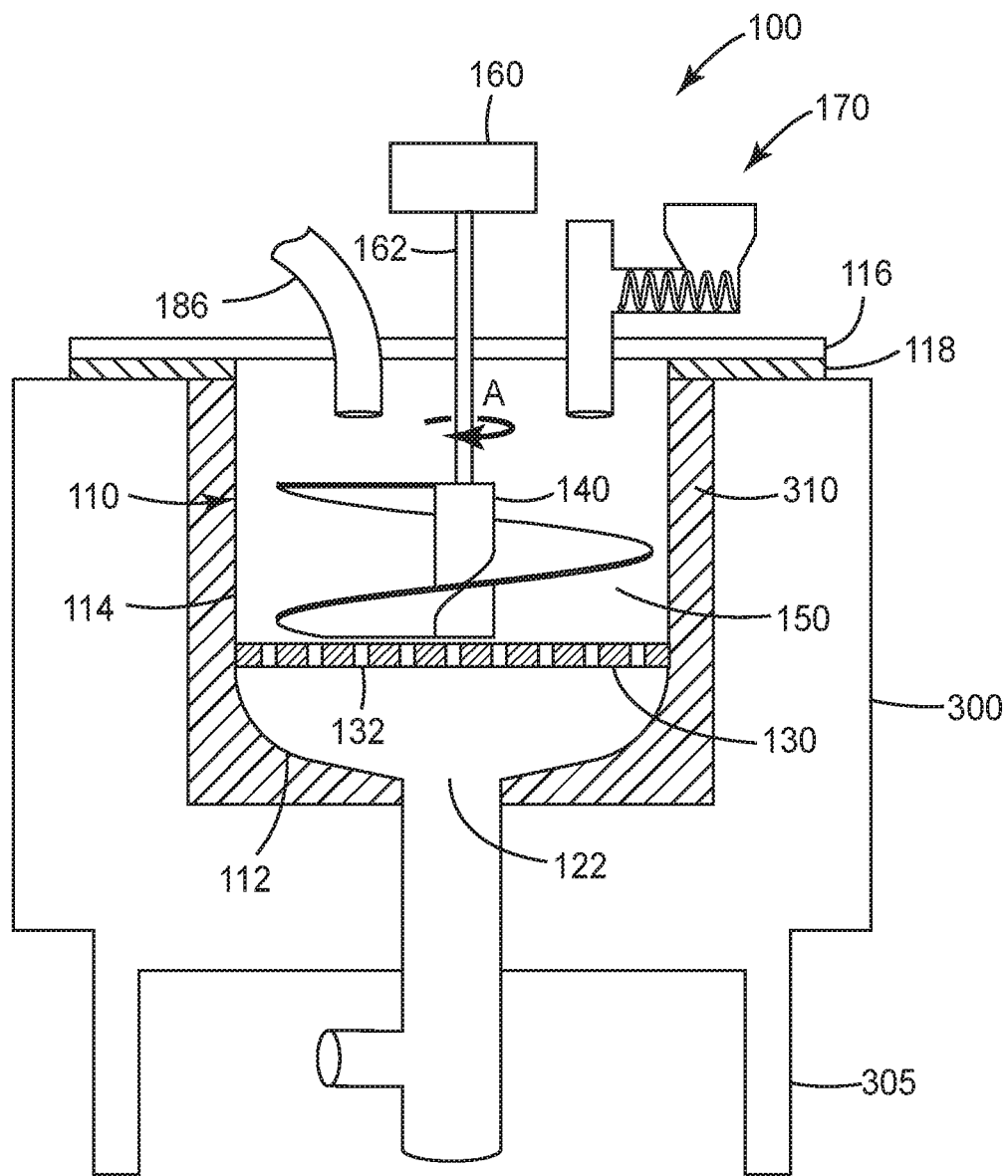
FIG. 2 illustrates the MSRB of FIG. 1, including an optional support structure.
Figure 3:
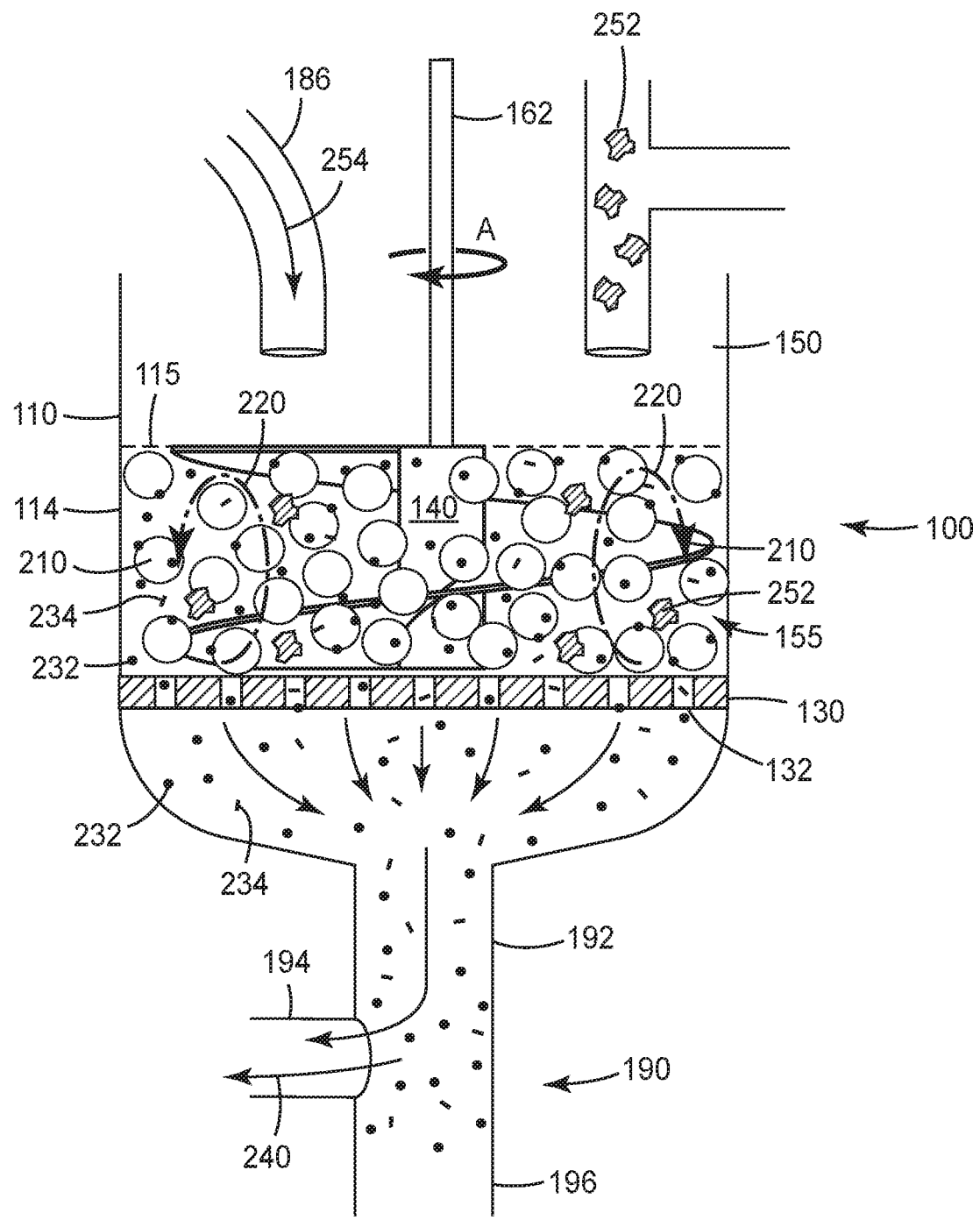
FIG. 3 illustrates the MSRB of FIG. 1 as operated according to some embodiments of the present disclosure.

The present inventors have developed mechanical stirred bed reactors that can be used for the upcycling of such perfluoropolymers. Referring to FIGS. 1 to 3, mechanical stirred bed reactor ("MSBR") 100 includes reaction chamber 110 comprising bottom wall 112, and one or more side walls 114 extending from the bottom wall. Agitator 140 is located within reaction chamber 110 and is connected by drive shaft 162 to motor 160. As shown in FIG. 2, MSBR 100 may be supported by structure 300, which may include legs 305. MSBR 100 may also include external heating system 310 used to heat the contents of the MSBR. Cover 116 is located over the top perimeter of the side walls and may be attached to support 300. Optional seal 118 can be included to help seal the space between the cover and the support.

Although the shape of the side wall(s) 114 is not particularly limited, a continuous, rounded side wall is preferred to avoid corners and dead spots in the reaction chamber. In some embodiments, the side wall is circular, and the reaction chamber is cylindrical. In some embodiments, bottom wall 112 slopes toward discharge port 122 to aid in removal of the filler materials, as discussed below.

MSBR 100 also includes screen 130 (sometimes referred to as a sieve) suspended above bottom wall 112. Screen 130 includes a plurality of openings 132. The total reactor volume 150 of the mechanical stirred bed reactor is defined as the volume of reaction chamber 110 contained within side wall 114 and extending from screen 130 to the top of the side wall.

As shown in FIG. 3, reaction chamber 110 is filled with beads 210 to a height shown by fill line 115. The portion of total reactor volume 150 that is filled by the beads is referred to as active reaction volume 155, which corresponds to the volume bounded by side wall 114 and extending from screen 130 to fill line 115. Generally, the greater efficiencies that can be achieved with higher active reaction volumes must be balanced against the power required to rotate agitator 140 in the bed of beads 210 to achieve the desired bed circulation, which includes both radial motion and axial mixing. In some embodiments, active reaction volume 155 is at least 20%, e.g., at least 30% or even at least 50% of total reactor volume 150. In some embodiments, beads 210 are loaded into the reactor to achieve an active reaction volume 155 of no greater than 95%, e.g., no greater than 90, or even no greater than 80% of total reactor volume 150. In some embodiments, the active reaction volume is 20 to 95%, e.g., 30 to 90 vol %, 30 to 80 vol %, or even 50 to 80 vol. % of the total reactor volume.

Feed system 170 is used to feed the perfluorinated polymer material into the reaction chamber for pyrolysis. Any known feed system may be used including, e.g., screw extruders, injection gases, and vibratory feeders. Exemplary feed system 170 includes hopper 172 for holding material to be fed, feed tube 176 extending into reaction chamber 110 through feed port 178, and conveyor 174 to move material from the hopper to the feed tube. Although the MSBR can be used for batch operations, in some embodiments, the feed system may be designed to provide a continuous feed of material to the reaction chamber for processing. The feed system may include any known systems for starting and stopping the flow of feed, and for controlling the feed rates.

Carrier gas system 180 is used to introduce gas into the reaction chamber. Together with discharge system 190, the carrier gas system provides the desired flow of gas through the reaction chamber of the MSBR. Any known carrier gas system may be used. Exemplary carrier gas system 180 includes gas source 182 and gas tube 186 extending into reaction chamber 110 through gas port 188. In some embodiments, the gas source may be pressurized to deliver gas through the gas tube. Although not shown, alternatively or additionally, carrier gas system 180 may include a mechanism, for example a pump or blower, to aid in delivering the carrier gas. The carrier gas system may also include any known systems for controlling the start, stop, and flow rate of carrier gas into the reaction chamber.

The carrier gas should not detrimentally affect the pyrolysis reactions or the materials in the reaction chamber. Therefore, in some embodiments, the carrier gas is steam or an inert gas, e.g., nitrogen or a noble gas. In some embodiments, superheated steam (e.g., steam at temperature of at least 150° C., e.g., 150 to 700° C.) may be used as the carrier gas as this can be source of additional energy to raise and maintain the temperature in the reaction zone. In some embodiments, reactive gases may be present, e.g., fluorine-containing gases such as R22 or R23 may be included. Such gases may also decompose under the pyrolysis conditions to generate additional perfluorinated olefin monomers (e.g., TFE and HFP). Combinations of gases, e.g., a combination of nitrogen and superheated steam may be used as the carrier gas.

Generally, the flow rate of the carrier gas can be used to control the residence time, the conversion percentage, and the ratio of the perfluorinated olefin monomers produced. For this reason, the carrier gas flow rate is usually expressed as the number of reactor volumes per unit time, so that the desired flow rates can be scaled with reactor volume. In the present reactor design the relevant volume is the active reaction volume. In some embodiments, the carrier gas flow rate is at least 0.01, e.g., at least 0.1 or even at least 1 active reaction volume per minute. In some embodiments, the gas flow rate is no greater than 100, e.g., no greater than 50 active reaction volumes per minute. In some embodiments, the carrier gas flow rate ranges from 0.01 to 100, e.g., 0.1 to 10 active reaction volumes per minute.

Discharge system 190 includes discharge tube 192 extending from bottom wall 112. In some embodiments, the discharge tube includes product branch 194 and filler branch 196. In operation, the pyrolysis gases can be removed through product branch 194, while the solid fillers that pass-through openings 132 in screen 130 can be collected through filler branch 196. As shown, the optional slope in bottom wall 112 can aid in delivering filler to discharge tube 192. In some embodiments, the discharge system may include a vibration or mechanical system to propel the solid fillers along the bottom wall and through the discharge system.

In some embodiments, the discharge system may include a mechanism, e.g., a vacuum pump, to aid in pulling the carrier gas and pyrolysis gases through the reaction chamber. Such a mechanism may be used in place of or in addition to a pressurized gas source and/or the mechanisms (e.g., blowers) used to aid in delivering the carrier gas into the reaction chamber.

As feed 252 is delivered into reaction chamber 110, agitator 140 mixes the feed with beads 210. In some embodiments, agitator 140 can be designed and operated to create flow patterns (shown by arrows 220) lifting the beads and feed materials up from screen 130, toward the top of active reaction volume 155, out toward wall 114, and down toward screen 130. In this way, the entire bed can be agitated to enhance heat transfer and facilitate the efficient pyrolysis of the feed. Agitator 140 can be designed and operated to create other flow patterns, provided efficient mixing of at least 90, or even 100% of the bed is achieved.

To achieve the desired mixing efficiency, the dimensions of the agitator can be selected relative to the dimensions of the reaction chamber so that the design of the mechanical stirred bed reactor can be scaled. In some embodiments, the length of the agitator is at least 80%, e.g., at least 100% of the depth of the beads forming the active reactor volume. Generally, the bottom of the agitator may be positioned close to, but slightly above the screen to optimize mixing while avoiding damage or the inhibition of gas flow from the reactor (e.g., from 1 to 5 mm above the screen, or even from 2 to 3 mm above the screen. Similarly, the diameter of the agitator (measured at the outermost tips of the agitator) relative to the diameter of the reaction chamber may be selected such the tips of the agitator are positioned close to, but slightly separated from the reactor wall. In some embodiments, the tips of the agitator are positioned 10 to 30 mm from the reactor walls, e.g., from 15 to 25 mm from the reactor wall.

Figure 4:
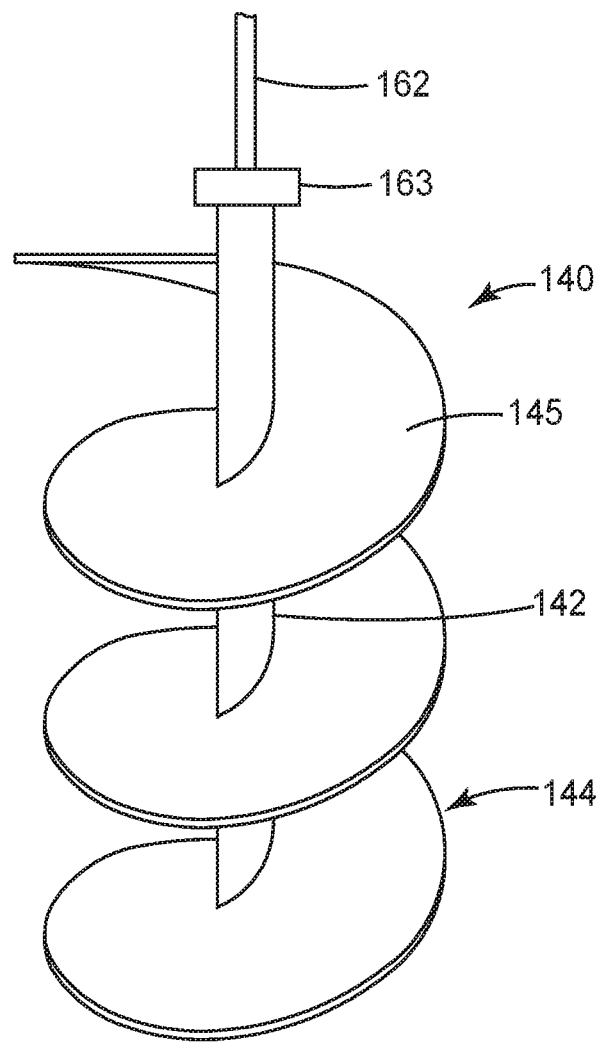
FIG. 4 illustrates an exemplary agitator according to some embodiments.

As shown in FIG. 4, in some embodiments, agitator 140 includes screw 144 comprising screw thread 145 surrounding agitator shaft 142. In some embodiments, the agitator shaft may be an extension of the drive shaft. However, in some embodiments, agitator shaft 142 may be connected, e.g., removably connected, to drive shaft 162 by, e.g., coupling 163.

Generally, the shape and dimensions of the screw threads and the direction of rotation can be selected to achieve the desired flow patterns. For example, in some embodiments a helical screw design may be used. In some embodiments, additional mixing blades may be attached to the shaft below the main agitator, (e.g., a screw) to assist in agitating and lifting material close to the surface of the screen. In either case, the bottom of the agitator may be positioned 1-5 mm above the screen, e.g., from 2 to 3 mm above the screen. Similarly, the diameter of the screw (measured at the outermost tips of the screws) relative to the diameter of the reaction chamber may be selected such the tips of the screw are positioned close to, but slightly separated from the reactor wall. If present, the mixing blades may also have a diameter such that the tips of the blades are positioned close to, but slightly separated from the reactor wall.

The design of the screw is not particularly limited. However, in some embodiments, the blade angle at the bottom of the screw is in the range of 10 to 35 degrees. In addition, in some embodiments, the screw thread forms at least one period of rotation about the shaft, e.g., at least two periods. The maximum number of periods will depend on the length of the screw and the blade angle, which may vary along the length of the agitator shaft.

The beads used to fill the reaction chamber can have a significant impact on energy consumption and pyrolysis efficiency. For example, to minimize the energy required to agitate the bed, larger, lighter weight beads may be desired. However, to maximize heat transfer from the beads to the feed and improve pyrolysis efficiency, smaller beads may be useful. In addition, beads having a higher thermal conductivity and higher heat capacity are preferred. Also, abrasion resistant beads are preferred to minimize or avoid damage to the beads during extended agitation as the beads repeatedly impact against each other, the agitator, and the reactor walls.

Relevant thermal properties of the beads include maximum use temperature, thermal conductivity, and heat capacity. Pyrolysis to decompose fluoropolymers into perfluorinated olefin monomers (e.g., TFE and HFP) is typically performed at temperatures of 450 to 900° C., for example, 500 to 800° C. As a result, the maximum use temperature of the materials used to form the beads should be greater than 900° C. In some embodiments, the maximum use temperature is at least 1000° C., at least 1100° C., or even at least 1200° C.

To provide efficient heat transfer from the beads to the feed material, the thermal conductivity of the beads should be at least 2 watts per meter·Kelvin (2 W/mK), e.g., at least 3 W/mK. However, much higher thermal conductivities may be desired. Therefore, in some embodiments, the thermal conductivity of the beads is at least 50, e.g., at least 80 or even at least 100 W/mK. Generally, there is no upper limit on the thermal conductivity, except as may arise from material limitations. For example, in some embodiments, the thermal conductivity is no greater than 300 W/mK, e.g., no greater than 200 W/mK. In some embodiments, the average thermal conductivity ranges from 50 to 300, e.g., from 80 to 200, or from 120 to 150 W/mK. Exemplary materials having suitable thermal conductivities include stainless steel, $SiO_2$, $ZrSiO_4$, $Al_2O_3$, AlN, SiC, $Si_3N_4$, and pyrolysis coke (e.g. CARBOLUX SK, from CS Additive.)

Bead materials with high heat capacities can be beneficial to minimize cold spots in the bed and maintain high temperature differentials between the beads and the feed materials. In some embodiments, the beads have a heat capacity of at least 300 J/kg·K, e.g., at least 400, or even at least 700 J/kg·K. Generally, there is no upper limit on the heat capacity; however, in some embodiments, the materials have a heat capacity of 300 to 1500 J/kg·K, e.g., 500 to 1200 J/kg·K.

Relevant mechanical properties of the beads include density and durability (e.g., hardness or fracture toughness). Generally, the minimum density of the beads is based on the range of available materials meeting the desired thermal properties. As a result, the density of the beads is typically at least 1 gram per cubic centimeter (1 gm/cc). To provide energy efficient agitation, in some embodiments, the density of the bead is less than 6 g/cc, e.g., no greater than 4 g/cc or even no greater than 3 g/cc. In some embodiments, the average density of the beads is between 1 and 4 g/cc, e.g., between 1 and 3 g/cc, or even between 1.5 and 2.5 g/cc.

To minimize the risk of damaging the beads during agitation, the hardness and fracture toughness of the beads may be used to guide the selection of materials. In some embodiments, the fracture toughness (K1c) is at least 2 MPa·m$^{1/2}$. In some embodiments, the fracture toughness is at least 3, at least 4 or even at least 6 MPa·m$^{1/2}$. In some embodiments, even higher fracture toughness may be desired for example at least 8 or even at least 9 MPa·m$^{1/2}$. Although less relevant, hardness can also contribute to prolonged life of the beads. In some embodiments, the hardness (Vickers HV 1) of the beads is at least 5 GPa, e.g., at least 10 GPa.

Metals can have very high thermal conductivities (e.g., 200-300 W/mK); however, they tend to have higher densities and lower maximum use temperatures than ceramic materials. Therefore, although metals beads such as stainless steel may be suitable for some applications, in some embodiments, ceramic beads may be preferred. Exemplary ceramic materials include oxide ceramics (e.g., $ZrSiO_4$, $Al_2O_3$, and $SiO_2$) and non-oxide ceramics (e.g., BC, SiC, AlN, and $Si_3N_4$). In some embodiments, beads comprising or consisting of carbon or pyrolysis coke (e.g., coke resulting from the pyrolysis of acetylene) may be used. In some embodiments, beads comprising both carbon and ceramic may be used. Representative properties of beads that may be preferred in some applications are summarized in Table 1.

TABLE 1

General properties of exemplary bead materials.

| Material | Density (g/cc) | Thermal Conductivity (W/mK) | Heat Capacity (J/kg · K) |
| --- | --- | --- | --- |
| Stainless steel | 7.9 | 20 | 500 |
| SiC | 2.8 | 85-120 | 1125 |
| $ZrSiO_4$ | 4.1 | 3-4 | 27 |
| $Al_2O_3$ | 3.9 | 35-39 | 990 |
| AlN | 3.3 | 70-285 | 738 |
| $Si_3N_4$ | 3.4 | 15-25 | 500-900 |
| $SiO_2$ | 2.2-2.7 | 0.3 | 835 |
| Graphite/pyrolysis coke | 1.8 | 120-150 | 700 |

Generally, the shape of the beads may be selected to achieve desired mixing efficiency, thermal transfer, and packing density. In some embodiments, the beads are spheroidal. Spherical beads have a uniform cross-sectional dimension (diameter). However, variations from a spherical shape can be tolerated. Therefore, as used herein, the term "spheroidal" includes beads having a major axis and a minor axis, where the ratio of the minor axis (or "minimum dimension") over the major axis (or "maximum dimension") is at least 0.5, e.g., at least 0.8, or even at least 0.9. Of course, the term spheroidal also include spherical beads, i.e., where the ratio of major axis over minor axis is 1.0. In addition, the term "spheroidal beads" includes beads having smooth surfaces as well as those having surface roughness.

Generally, the size of the beads is not particularly limited. However, the selection of the minimum dimension of the beads will be affected by the dimensions of the filler material in the fluorinated feed materials. In operation, the openings in the screen must be large enough to permit the filler materials to pass through, but small enough to prevent the beads from passing though.

Figure 5:
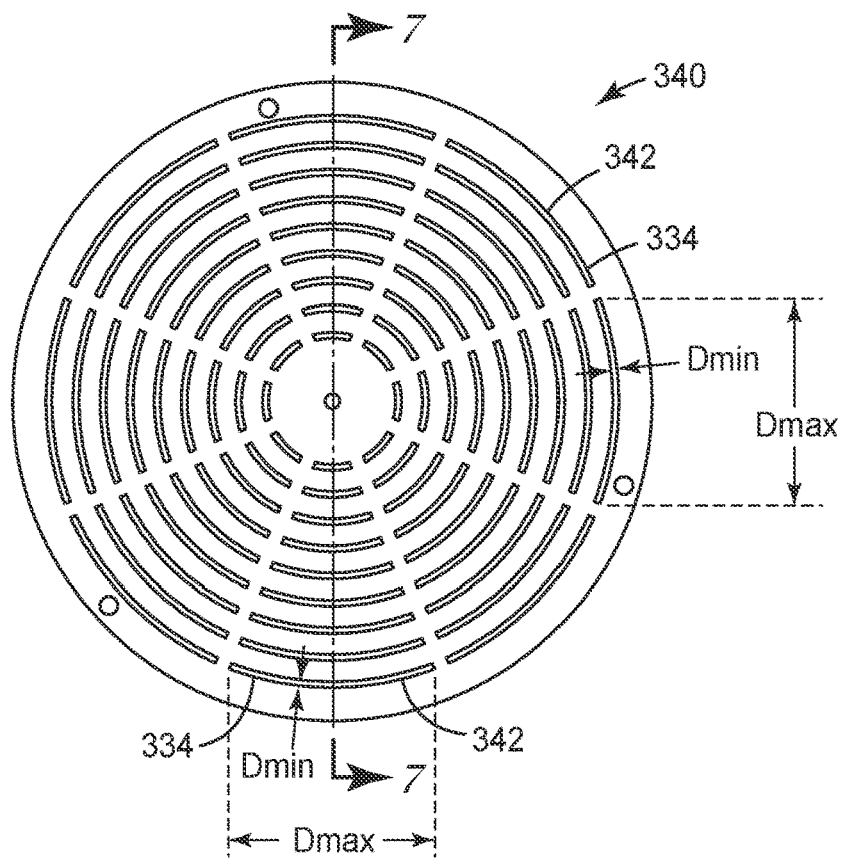
FIG. 5 illustrates one exemplary screen of the present disclosure.
Figure 6:
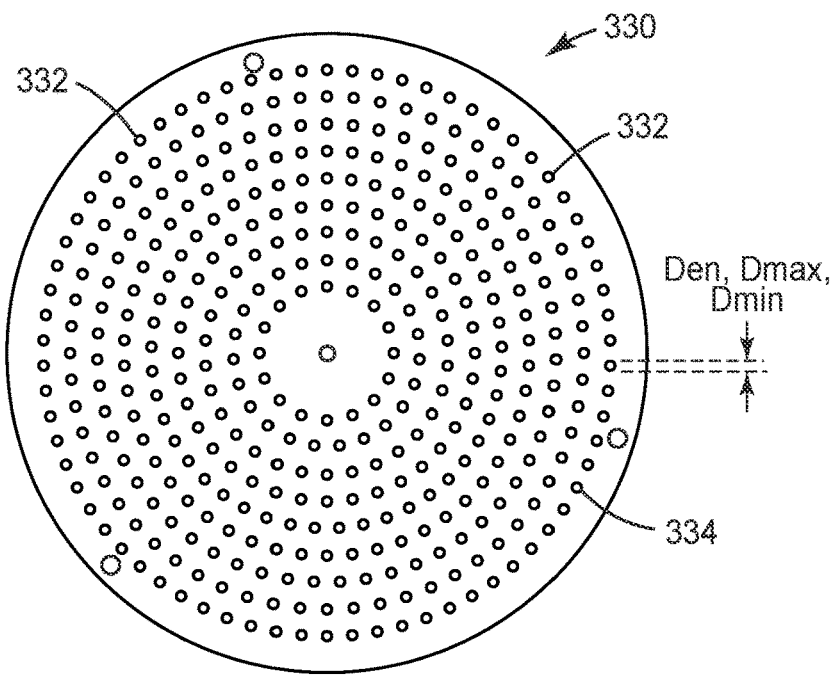
FIG. 6 illustrates another exemplary screen of the present disclosure.

Top views of two exemplary screens are shown in FIGS. 5 and 6. As shown in FIG. 6, in some embodiments screen 330 includes a plurality of openings 332 having a circular entrance 334 with a diameter, Den. As the openings are circular, both the major dimension (Dmax) and minor dimension (Dmin) of entrance 334 are equal to diameter Den. In some embodiments, non-circular entrance shapes may be used, e.g., squares, rectangles, polygons, or even random shapes. For example, referring to FIG. 5, in some embodiments, openings 342 of screen 340 are slot shaped (e.g., curved slots) and entrance 334 of openings 342 have a major dimension (Dmax) that is greater than minor dimension (Dmin).

The open area of the screen is defined as the cumulative area of the entrances of all openings. This can be expressed as a percentage of the total area of the top surface of the screen. Greater filler removal efficiency can be achieved with higher open areas. However, this should be balanced against the need for sufficient structural integrity to support the bed of beads at the operating temperatures. In addition, in some embodiments, a smaller percent open area may be beneficial as the greater thermal mass of such a screen can help retain the desired reaction temperatures. In some embodiments, the open area as a percent of the total area is at least 20%, e.g., at least 30, or even at least 40%. The maximum allowable percent open area will be related to the thermal and mechanical properties of the materials used to make the screen. Screen designs can include structural support elements allowing greater open areas. In some embodiments, the percent open area is no greater than 80%, or even no greater than 70%.

In some embodiments, e.g., when circular openings are used, the minimum dimension of the entrance to the openings (Dmin) is greater than the maximum dimension of the filler (Dfill). If the filler includes a variety of filler materials and/or a range of filler sizes, Dmin is greater than the maximum dimension of at least 80 wt. % of the fillers, e.g., at least 90 wt. %, or even 95% of the fillers. In some embodiments, e.g., when slot-shaped opening are used, the minimum dimension of the entrance to the openings (Dmin) may be less than the maximum dimension of the filler (Dfill); provided the maximum dimension of the opening (Dmax) is greater than the maximum dimension of the filler. For example, with fiber fillers having a length and a diameter, the fibers may pass through slots so long as the maximum dimension of the slots is greater than the length of the fibers, and the minimum dimension of the slots is greater than the diameter of the fibers. However, as the fibers may align at angles relative to the slots, even with fiber fillers, it is preferred that the minimum dimension of the entrance to the openings be greater than the maximum dimension of the fillers.

Generally, the dimension of the openings can be selected from the expected range of filler sizes. In some embodiments, the ratio of minimum dimension of the entrance to the openings (Dmin) over the maximum dimension of the fillers (Dfill) is at least 1.5. However, to improve removal efficiency and minimize plugging of the openings, in some embodiments, the ratio of Dmin/Dfill is at least 5, at least 10, or even at least 20. As the openings must remain small enough to prevent the loss of the beads of the reactor bed, larger screen openings will require the use of larger beads. Therefore, in some embodiments, the ratio of Dmin/Dfill is no greater than 100, e.g., no greater than 50, or even no greater than 30.

Figure 7:
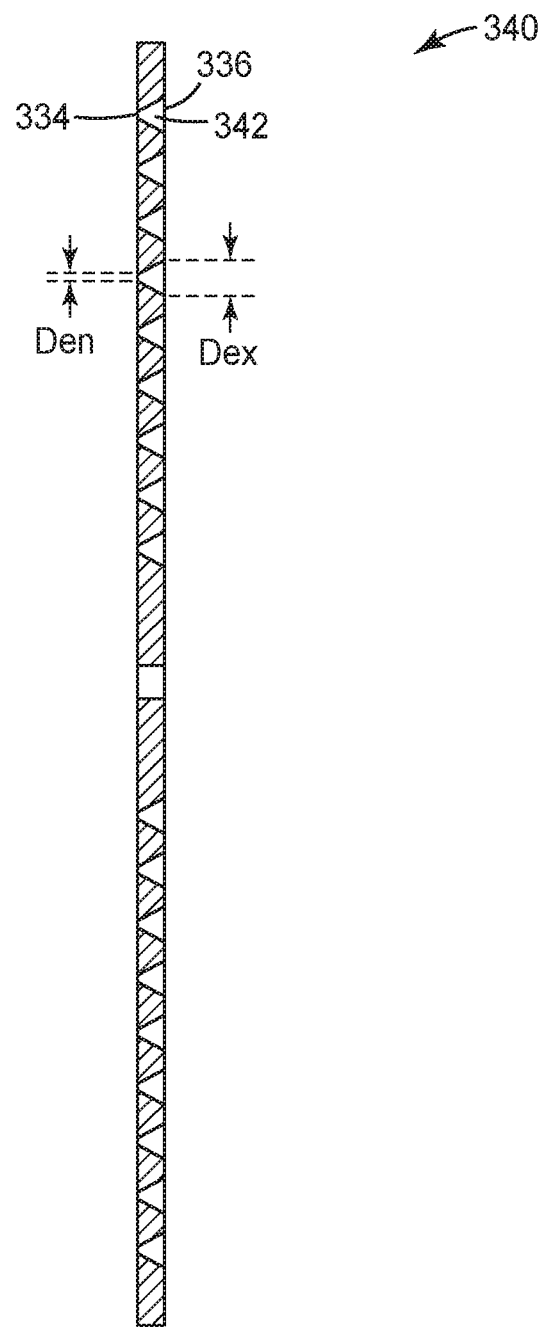
FIG. 7 illustrates a cross-sectional view of the screen of FIG. 5.

In some embodiments, the openings have a constant cross-section through the thickness of the screen. Thus, an opening having a circular entrance would be a cylinder with a circular exit of the same size as the entrance. However, in some embodiments, it may aid in preventing blocking and increasing the efficiency of filler removal if the openings increase in size from the entrance to the exit. FIG. 7 is a cross-section of screen 340 of FIG. 5. As shown, openings 342 have entrance 334 with a minimum dimension at the entrance of Den. The minimum dimension of openings 342 increases through the thickness of the screen from Den until reaching Dex at the exit 336 of the opening, where Dex is greater than Den. In some embodiments, the ratio of Dex over Den is at least 1.5, e.g., at least 2 or even at least 4. In some embodiments, the ratio of Dex over Den is between 1.5 and 5, e.g., 1.5 to 4, or 2 to 4, inclusive. With a circular entrance and exit, the resulting openings are conical, however other shapes are possible. For example, the openings may increase in size from the entrance to the exit while changing cross-section shape from a circle to, e.g., a square.

Once the minimum dimension of the entrances to the openings in the screen is selected, the dimensions of the beads forming the bed in the reactor can be selected. Generally, to retain the beads in the reactor, the minimum dimension of the entrance must be less than the maximum dimension of the beads, Dbead. For spherical beads, this means the diameter of the beads must be greater than minimum dimension of the entrance to the openings. In some embodiments, the ratio of the Dbead over the minimum entrance dimension (Dmin) is at least 1.5, e.g., at least 3, or even at least 5. However, to minimize the risk of lost beads and to improve mixing efficiency, larger bead sizes may be desired. In some embodiments, the ratio Dbead over Dmin is at least 5, e.g., at least 10, or even at least 20. As larger bead diameters may result in less efficient thermal transfer, in some embodiments, the ratio of Dbead over Dmin is no greater than 50, no greater than 30, or even no greater than 20.

Following these guidelines, one of ordinary skill in the art can select the dimensions of the beads and screen openings based on the dimensions of the fillers. For example, glass and carbon fibers are a common filler used with fluoropolymers. Such fibers may have a fiber diameter of 10 to 15 microns and an average fiber length of 50 to 60 microns. Other common fillers include glass or ceramic spheres, and irregular shaped fillers such as metal or ceramic flakes. The maximum dimension of such fillers may range from less than 1 micron to as large as, e.g., 25, 50 or even 100 microns. However, larger or smaller fillers (fibers or particles) may be present.

Depending on the expected maximum size of the fillers (Dfill), the minimum dimension of the entrances to the screen openings (Dmin) can be selected. For example, in some embodiments, Dmin may be at least 50 microns, e.g., at least 100, or even at least 250 microns. In some embodiments, Dmin may be at least 500, or even 1000 microns.

The size of the beads will then depend on the size of the openings in the screen. In some embodiments, the beads may range in size (i.e., maximum cross-sectional dimension or diameter of the bead, Dbead) from, e.g., 100 microns to 30 mm. In some embodiments, to assist in retaining the beads on the screen, the maximum cross-sectional dimension the bead is at least 200 microns, or even at least 0.5 mm. In some embodiments, the maximum cross-sectional dimension of the beads is no greater than 20 mm, or even no greater than 10 mm. For example, in some embodiments, the beads range in size from 200 microns to 10 mm, or even from 1 mm to 10 mm.

The selection of the relative dimensions of the filler, screen openings, and beads can be selected based on a variety of factors. For example, the fillers may have a range of sizes. As used herein, DF95 is defined such that 95% by mass of the fillers have a maximum dimension of less than or equal to DF95. Similarly, the beads may have a range of sizes. As used herein, DB5 is defined such that no greater than 5% by mass of the beads have a maximum dimension of less than DB5. The minimum dimension of the entrance to the openings can then be selected based on these parameters. For example, if Dmin is greater than DF95, at least 95% by mass of the fillers can pass through the screen. Similarly, if Dmin is less than DB5, no greater that 5% by mass of the beads might be lost through the screen. Further exemplary dimensions and ratios based on DF95 and DB10 are provided in Table 2. In this table, Dmin refers to the minimum dimension of the entrance to the openings in the screen.

TABLE 2

Exemplary dimensions for a MSBR.

| Filler DF95 (microns) | Dmin/DF95 | Opening Dmin (mm) | DB5/Dmin | Bead DB5 (mm) |
|---|---|---|---|---|
| 60 | 5 | 0.3 | 5 | 1.5 |
|  |  |  | 10 | 3 |
|  |  |  | 20 | 6 |
|  | 10 | 0.6 | 5 | 3 |
|  |  |  | 10 | 6 |
|  |  |  | 20 | 12 |
|  | 20 | 1.2 | 5 | 6 |
|  |  |  | 10 | 12 |
|  |  |  | 20 | 24 |
| 100 | 5 | 0.5 | 5 | 2.5 |
|  |  |  | 10 | 5 |
|  |  |  | 20 | 10 |
|  | 10 | 1 | 5 | 5 |
|  |  |  | 10 | 10 |
|  |  |  | 20 | 20 |
|  | 20 | 2 | 5 | 10 |
|  |  |  | 10 | 20 |
|  |  |  | 20 | 40 |

In order to decompose the fluoropolymer feed into the desired perfluorinated olefin monomers (e.g., TFE and HFP), the reaction volume should be heated to and held at a temperature of at least 450° C. In some embodiments, higher temperatures, e.g., 500, 800 or even 900° C. may be preferred. Referring to FIG. 2, in some embodiments, at least a portion of the energy used to heat the beads of the reactor bed can be supplied by external heating system 310 surrounding at least a portion of reaction chamber 110. Any known heating system may be used including electrical, gas, and steam heaters.

In some embodiments, alone or in addition to such heating systems, microwave energy may be used to heat the reactor bed. To increase the efficiency of microwave heating, in some embodiments, the beads themselves may be made of a microwave active material. In some embodiments, microwave active material may be included with the beads in the reactor bed. For example, in some embodiments, the at least 20%, e.g., at least 30% or material forming the reactor bed comprises microwave active material.

Microwave active materials heat up upon irradiation by microwaves. Typically, microwave active materials heat up by at least 10° C., preferably by at least 20° C., and more preferably by at least 30° C., when submitting one gram of the microwave active material at ambient conditions to microwave irradiation of 0.7 kW for 5 minutes.

Generally, the dimensional requirements of such microwave active materials are similar to those imposed on the beads so that they are not lost through the openings in the screen. The microwave active material should also meet similar density and use temperature requirements as the beads. Generally, the microwave active beads are solid at the decomposition temperature of the fluorinated material. In some embodiments, the microwave active beads have a melting point or decomposition point of greater than 800° C., greater than 10000° C., or even greater than 1500° C.

Suitable microwave materials and systems are described in e.g., U.S. Pat. No. 8,344,190. Microwave active materials include those comprising, for example, carbon, graphite, carbides, silicides, borides, nitrides, metal oxides, metal hydroxides, metal halides, in particular metal chlorides, and metal fluorides. Further microwave active materials also include those comprising metals, such as, for example, Ni, Pt, Co, Pt, metal alloys such as, for example, Pt/Cu, Pt/Re alloys, chromates, and titanates. Combinations and blends of microwave active materials may be used.

In some embodiments, the reactor may contain or may be connected to a plasma zone. The plasma zone is typically located at, or after the active reaction volume (also referred to and the decomposition zone) of the MSBR. The plasma may accelerate the decomposition reactions used to generate the perfluorinated olefin monomers. When used after the decomposition zone, the plasma may prevent or reduce precipitation of fluorocarbon particles and repolymerization of the perfluorinated olefin monomers generated during decomposition.

The plasma may be generated, for example through, microwave irradiation, by electric arcs, such as those described in international patent application WO 01/58840 to Van der Walt et al., or by corona treatment. The energy level of the plasma zone can be optimized to stabilize the plasma but to prevent or reduce the deposition of fluorocarbon particles by minimizing the decomposition of fluoroolefins monomers. The energy level required to generate and stabilize the plasma may depend on the composition and amounts of the product gas, the carrier gas, and any other gaseous reaction media.

In some embodiments, the mechanical stirred bed reactor may also contain or may be connected to a quenching zone. The quenching zone is located after the decomposition zone. If a plasma zone is located after the decomposition zone, the quenching zone is typically located after that plasma zone. The hot product gases generated by the decomposition of the fluorinated material contains the perfluorinated olefin monomers. These product gases are quenched to stabilize the newly formed products and prevent or reduce repolymerization of the perfluorinated olefin monomers. Typically, quenching involves cooling the gas from a temperature of greater than 400° C., typically from about 400° C. to about 650° C., to a temperature below 250° C. in less than 5 seconds, preferably less than 1 second. Any suitable quenching system may be used, including, but not limited to, the expansion of the product gas stream, gas quenching by means of another gas which is cold, quench probes, such as, for example those described in international patent application WO 01/58840 to Van der Walt, or a combination thereof.

A variety of fluorocarbons may form as products from the decomposition reactions and may be present in the product gas. The desired perfluorinated olefin monomers, in particular, TFE and/or HFP, may be separated by conventional gas separation systems, including, e.g., condensation, expansion and distillation.

Exemplary methods of upcycling filled perfluoropolymers according to some embodiments of the present disclosure are described with reference to FIG. 3. Reaction chamber 110 of mechanical stirred bed reactor 100 is filled with beads 210 up to fill line 115 providing an active reaction volume of 155. The size of beads 210 and the dimensions of openings 132 in screen 130 are selected such that the beads do not pass through the openings.

Feed 252 comprising one or more perfluoropolymers, which may include any of a variety of fillers, is fed into reaction chamber 110 while agitator 140 is rotated in the direction shown by arrow A. Simultaneously, carrier gas 254 is fed into the reaction chamber where it flows through the active reactor volume, through openings 132 and out through discharge system 190.

As agitator 140 rotates, the beads and feed are mechanically agitated, following, e.g., the flow patterns indicated by arrows 220. Energy supplied by external heaters, microwave radiation (with or without microwave active particles), and/or carrier gas 254 (e.g., superheated steam) is sufficient to pyrolyze the feed, decomposing the fluoropolymers into perfluorinated olefins such as TFE and HFP. These products pass through openings 132 and, along with carrier gas 254, can be collected through product branch 194 for collection or further processing.

As the fluoropolymers decompose, the fillers (e.g., particles 232 and fibers 234) are released from the feed. The size of openings 132 allows the fillers to pass through screen 130, where they can be separated from the product stream and collected through filler branch 196.

The following examples illustrate methods of upcycling filled perfluoropolymers into perfluorinated olefin monomers using an exemplary mechanical bed stirred reactor according to some embodiments of the present disclosure.

Example 1. A mechanical stirred bed reactor corresponding to the design shown in FIG. 1 was used. The cylindrical reaction chamber had a ratio of diameter to height of 1:1. The screen was positioned above the sloped floor of the reaction chamber to provide a total reactor volume above the screen of 6 liters, while the total volume of the reaction chamber, including the space below the screen was 6.6 liters.

A screen generally corresponding to the design shown in FIG. 5 was used. The minimum dimension of the slot-shaped openings was 0.8 mm at the entrance of the screens. The minimum dimension of the slots increased through the thickness of the screen, reaching a width of 2.2 mm at the exit side of the screen.

Silicon carbide was screened and analyzed by the sieve analysis method DIN 66165 yielding beads having an average (d50) diameter of 3 millimeters. These beads were loaded into the reaction chamber to achieve an active reaction volume of 50% of the total reaction volume, i.e., approximately 3 liters. The beads surrounded an agitator having a helical screw forming two periods around its shaft. The angle of the helix was 10.3 degrees resulting in a thread pitch of 18%. The tips of the screw were positioned 20 mm from the reactor wall.

An external heater was used to raise the temperature of the bed to 620° C. prior to starting the flow of feed material. Superheated steam (250° C.) was used as the carrier gas and was blown into the reactor at a rate of 0.1 active reaction volumes per minute, i.e., approximately 0.3 liters/min. Then, over an eight-hour period, 2.1 kilograms of a perfluorinated polymer (polytetrafluoroethylene) containing 25 wt. % glass fibers (3M DYNEON PTFE TF 4105) was fed into the reactor. The feed material was about 1 mm in size. The glass fibers had an average length of about 50 microns and an average diameter of about 14 microns. The dimensions and relative dimensions of the beads, filler and screen openings are summarized in Table 3.

The agitator was rotated at a circumferential speed of 0.06 meter/second throughout the process, providing good circulation of the entire bed. The perfluorinated polymer feed was successfully upcycled to produce the desired perfluorinated olefin monomers. The product gas composition was 95 wt. % TFE, 4 wt. % HFP and 1 wt. % c-$C_4F_8$. The $CF_2$ yield was 88%. The filler was efficiently removed from the reactor, as greater than 70 wt. % of the glass fibers were removed from the bed and collected below the screen.

Example 2. The same equipment and procedures were used, except the pyrolysis temperature was 600° C. The feed was a mixture of PTFE with 20 wt. % of silver particulate filler having an average size of 10 microns. The dimensions and relative dimensions of the beads, filler and screen openings are summarized in Table 3. The product gas composition was 65 wt. % TFE, 16 wt. % HFP and 19 wt. % c-$C_4F_8$. The total yield of the products was 75 wt. %. Greater than 77 wt. % of the silver filler was removed from the reaction chamber and collected below the screen.

TABLE 3

Dimensions and relative dimensions

|  | Example 1 | Example 2 |
| --- | --- | --- |
| DFill | 50 microns | 10 microns |
| Dmin | 0.8 mm | 0.8 mm |
| DBead | 3 mm | 3 mm |
| Dmin/Dfill | 16 | 80 |
| Dbead/Dmin | 3.75 | 3.75 |

In Table 3, DFill refers to the maximum dimension of the filler, i.e., the length of the glass fibers or the diameter of the silver particles. The fibers and particles had a narrow size distribution, therefore, DFill is a close approximation of DF95 for each filler. Dmin refers to the minimum dimension of slot-shaped openings on the entrance side of the screen. DBead refers to the D50 value of the beads. As the beads had a very narrow size distribution, D50 is a close approximation of DB5 for the beads.

Suitable test methods for determining the values of various parameters discussed herein and recited in the claims are summarized in Table 4. All test methods refer to the version in effect on Jan. 1, 2020.

TABLE 4

Test methods.

| Parameter | Test method |
| --- | --- |
| Density of materials used to form the beads | DIN EN 623-2 |
| Thermal conductivity of materials to form the beads | DIN EN 821-2 |
| Heat capacity of materials to form the beads | DIN 821-3 |
| Distribution of particle size (D5, D50 and D95) | DIN 66165 |
| Distribution of fiber lengths (D5, D50 and D95) | ISO-22314 |

What is claimed is:

1. A method of converting a filled perfluoropolymer into perfluorinated olefins comprising:
   a) feeding a perfluoropolymer containing an inorganic filler into a reaction chamber of a mechanical stirred bed reactor comprising
      i) a bottom wall, a side wall connected to and extending from the bottom wall to a top of the side wall;
      ii) a screen comprising a plurality of openings extending through the screen from an opening entrance at the top side of the screen to an opening exit on the bottom side of the screen, wherein the screen is supported above the bottom wall and the reaction chamber has a total reaction volume bounded by the side wall and extending from the screen to the top of the side wall;
      iii) a bed of beads supported by the screen and filling at least 20% of the total reaction volume; and
      iv) an agitator comprising a screw thread surrounding an agitator shaft;

b) agitating at least 80 wt. % of the beads with the agitator while heating the perfluoropolymer to a temperature of at least 450° C. and passing a carrier gas through the beads;
c) decomposing the perfluoropolymer to form perfluorinated olefin monomers and releasing the filler; and
d) collecting the perfluorinated olefin monomers and the fillers below the screen;

wherein at least 95 wt. % of the filler has a maximum dimension of no greater than DF95, wherein no greater than 5 wt. % of beads have a maximum dimension of less than DB5; and wherein the minimum dimension of the openings in the screen on the side of the screen supporting the beads is Dmin; further wherein the ratio of Dmin over DF95 is at least 5, and the ratio of DB5 over Dmin is at least 1.5.

2. The method of claim 1, wherein the inorganic filler comprises inorganic fibers.

3. The method of claim 1, wherein the carrier gas comprises superheated steam.

4. The method of claim 1, wherein the ratio of Dmin over DF95 ranges from 10 to 100, inclusive.

5. The method of claim 4, wherein the ratio of DB5 over Dmin ranges from 3 to 10, inclusive.

6. The method of claim 1, wherein the beads comprise a ceramic.

7. The method of claim 1, wherein the beads comprise carbon.

8. The method of claim 1, wherein the beads are spheroidal and have a density of less than 6 grams per cubic centimeter and a thermal conductivity of at least 3 W/mK.

9. The method of claim 8, wherein the beads have an average density of 1.5 to 4 grams per cubic centimeter.

10. The method of claim 8, wherein the beads have an average thermal conductivity of 50 to 300 W/mK.

11. The method of claim 8, wherein the beads have a heat capacity of 300 to 1500 J/kg·K.

12. The method of claim 1, wherein the reactor further comprises microwave active material mixed with the beads and a source of microwave energy.

\* \* \* \* \*